United States Patent [19]

McKnight

[11] Patent Number: 5,042,466
[45] Date of Patent: Aug. 27, 1991

[54] WOUND DRESSING WITH TREATED RELEASE SHEET

[75] Inventor: James T. McKnight, Vernon Hills, Ill.

[73] Assignee: The Kendall Company, Mansfield, Mass.

[21] Appl. No.: 153,869

[22] Filed: Feb. 9, 1988

[51] Int. Cl.$^5$ .................... A61F 13/00; A61F 15/00
[52] U.S. Cl. .................................. 128/155; 206/441; 128/156
[58] Field of Search ............. 128/155, 156, 335; 206/440, 441; 604/304, 307

[56] References Cited

U.S. PATENT DOCUMENTS

| | | | |
|---|---|---|---|
| 2,646,040 | 7/1953 | Stanton | 128/155 |
| 3,313,405 | 4/1967 | Blackford | 206/441 |
| 4,513,739 | 4/1985 | Johns | 128/156 |
| 4,598,004 | 7/1986 | Heinecke | 128/156 |

FOREIGN PATENT DOCUMENTS

| | | | |
|---|---|---|---|
| 0117632 | 9/1984 | European Pat. Off. | 128/155 |
| 0842617 | 7/1960 | United Kingdom | 122/155 |

*Primary Examiner*—Randy Citrin Shay
*Assistant Examiner*—Paul Prebilic
*Attorney, Agent, or Firm*—Alvin Isaacs

[57] ABSTRACT

A wound dressing comprising, an elastomeric film permeable to water vapor and having adhesive on a front surface thereof. The dressing has a pair of release sheets extending to a central portion of the film to releasably cover the adhesive. The release sheets are treated throughout with a coating to permit release from the adhesive, with end margins only of the release sheets being additionally treated to more aggressively adhere to the adhesive than a central portion of the release sheets.

4 Claims, 1 Drawing Sheet

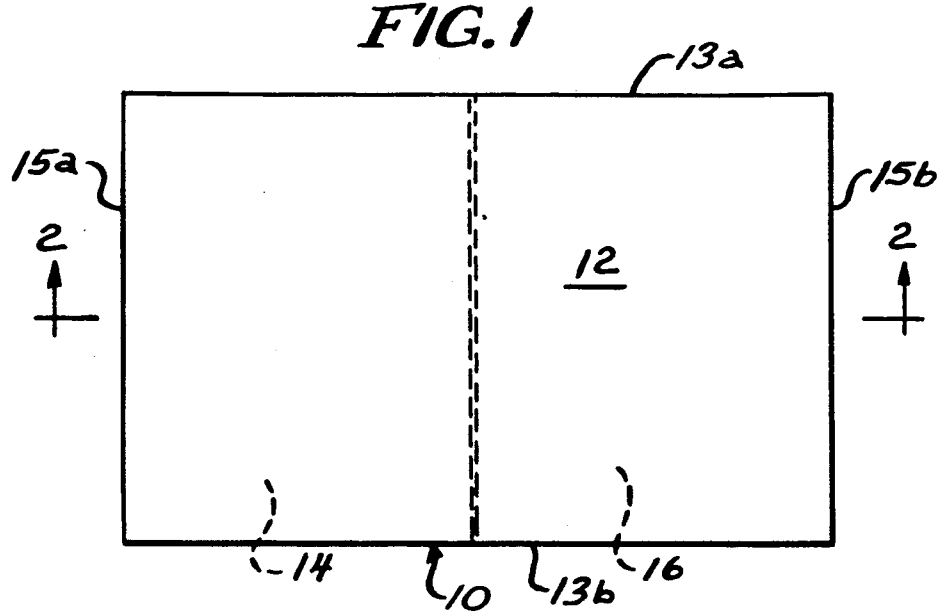
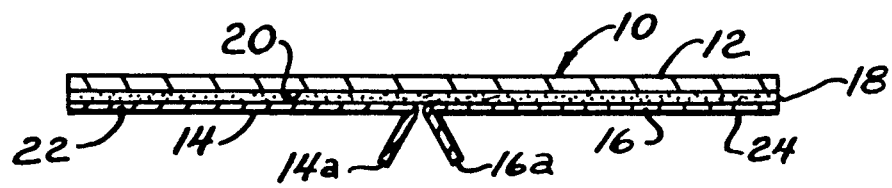
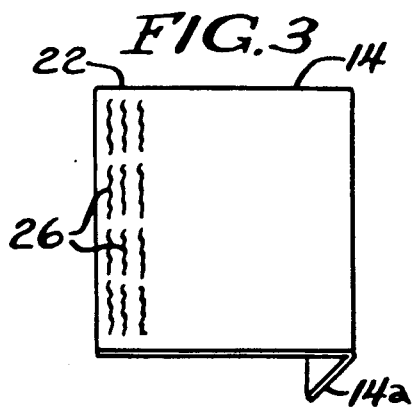
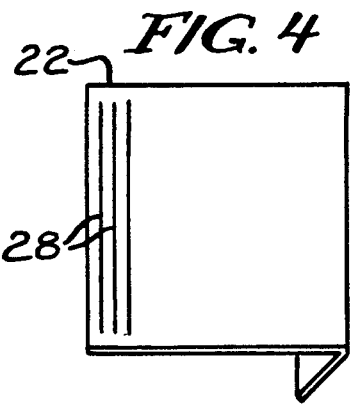
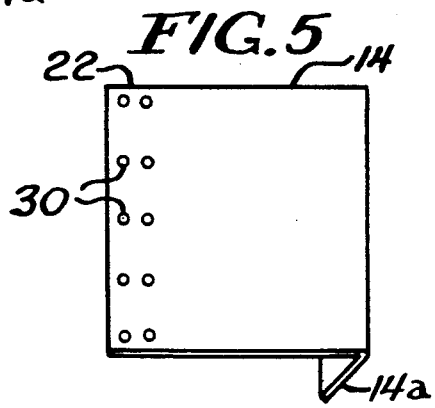

WOUND DRESSING WITH TREATED RELEASE SHEET

BACKGROUND OF THE INVENTION

The present invention relates to wound dressings.

An effective means of applying delicate adhesive coated film dressings to wounds consists of peeling back the release paper starting from the center of the dressing until a non-releasing strip is reached at the opposite edges of the dressing. The film is perforated at that point and these tabs including the release paper are torn off after the exposed adhesive surface is pressed onto the wound and the surrounding skin. These perforations are difficult to control to avoid lifting the adhesive film off parts of the skin along the perforated edge which will make that edge of exposed adhesive much more likely to catch and peel back further when rubbed by clothing. This non-releasing strip is normally produced by applying an adhesive coated paper tape to the adhesive coated film of the dressing so that the paper (non-release coating) contacts the adhesive on the film and the adhesive siding which is very aggressive, contacts the release paper in such a way that it is not released. This process is also difficult to control and requires additional materials.

Wound dressings are disclosed in U.S. Pat. Nos. 4,513,739 and 4,598,004.

SUMMARY OF THE INVENTION

A principal feature of the present invention is the provision of an improved wound dressing.

The dressing of the present invention comprises, an elastomeric film having adhesive on a front surface thereof, and release sheet means to releasably cover said adhesive.

A feature of the present invention is that the release sheet means has means on an end margin being treated to more aggressively adhere to the adhesive than a central portion of the release sheet means.

Thus, a feature of the present invention is that the release sheet means can be peeled to the end margins for placement of the film on a patient while the end margins retain the release sheet means to facilitate placement.

Further features will become more fully apparent in the following description of the embodiments of this invention and from the appended claims.

DESCRIPTION OF THE DRAWINGS

In the drawings:

FIG. 1 is a top plan view of a wound dressing of the present invention;

FIG. 2 is a sectional view taken substantially as indicated along the line 2—2 of FIG. 1; and FIGS. 3–5 are various embodiments of a release sheet for the dressing of FIG. 1.

DESCRIPTION OF THE PREFERRED EMBODIMENTS

Referring now to FIGS. 1 and 2, there is shown a wound dressing generally designated 10 having an elastomeric film 12 and a pair of release sheets 14 and 16 which extend to a central portion of the film 12. The film 12 has a pair of side edges 13a and 13b, and a pair of end edges 15a and 15b connecting the side edges 13a and 13b. The film 10 may be of any suitable type which is water vapor permeable, such as Polyskin, a Trademark of The Kendall Company having a polyester-polyether block polymer backing. This film 10 has a layer of adhesive 18 on a front surface 20 of the film 10. The adhesive may comprise suitable acrylic pressure sensitive adhesive. The release sheets 14 and 16 may have a suitable silicone release coating facing the adhesive 18 such that the release sheets 14 and 16 are releasably attached to the adhesive 18, and the release sheets 14 and 16 may have associated tabs 14a and 16a to facilitate their removal.

The release sheets 14 and 16 have end margins 22 and 24 at opposed ends of the film 10, and the end margins 22 and 24 of the release sheets are treated in a suitable manner to more aggressively adhere to the adhesive 18 than the central portion of the release sheets. For example, with reference to FIG. 3, the end margins of the release sheets have abraded regions 26 to accomplish this result. With reference to FIG. 4, the end margins of the release sheets have score lines 28 to accomplish this result. In the case of FIGS. 3 and 4, the adhesive flows into the exposed fibrous surface of the release sheets to increase the affinity of the release sheets to the adhesive 18. With reference to FIG. 5, the end margins of the release sheets may have perforations 30 to accomplish the same result as in FIGS. 3 and 4.

In use, the dressing 10 is placed over a wound of the patient, and the tabs 14a and 16a are grasped in order to peel the release sheets 14 and 16 from the adhesive 18 until the release sheets are peeled to the end margins 22 and 24. The end margins 22 and 24 of the release sheets hold the release sheets in place while the central portion of the film 12 is applied over the wound after which the release sheets are peeled from the adhesive 18, and the associated end margins of the film 12 can then be applied to the patient.

The foregoing detailed description is given for clearness of understanding only, and no unnecessary limitations should be understood therefrom, as modifications will be obvious to those skilled in the art.

I claim:

1. A wound dressing comprising:
   an elastomeric film having adhesive on a front surface thereof; and
   release sheet means to releasably cover said adhesive and being treated throughout with a release coating to permit release from the adhesive, with end margins only of the same release sheet means having means being additionally treated to more aggressively adhere to the adhesive than a central portion of the release sheet means,
   the additional treated means comprising scoring on said end margins or perforations in said end margins.

2. The dressing of claim 1 wherein said release sheet means comprises a pair of release sheets extending to a central portion of the film.

3. The dressing of claim 1 wherein the film is permeable to water vapor.

4. A wound dressing comprising:
   an elastomeric film having adhesive on a front surface thereof; and
   release sheet means to releasably cover said adhesive, with end margins of the release sheet means having means being treated to more aggressively adhere to the adhesive than a central portion of the release sheet means, wherein the treated means comprises abrasives on said end margins.

* * * * *